(12) United States Patent
Butters et al.

(10) Patent No.: US 7,790,883 B2
(45) Date of Patent: Sep. 7, 2010

(54) PROCESS FOR THE PREPARATION OF THIAZOLOPYRIMIDINES

(75) Inventors: Michael Butters, Bristol (GB); Richard Wisedale, Bristol (GB); Matthew James Welham, Bristol (GB); Colin Thompson, Loughborough (GB); Andrew Watts, Loughborough (GB)

(73) Assignee: AstraZeneca AB, Sodertalje (SE)

( * ) Notice: Subject to any disclaimer, the term of this patent is extended or adjusted under 35 U.S.C. 154(b) by 215 days.

(21) Appl. No.: 10/581,143

(22) Filed: Feb. 14, 2007

(65) Prior Publication Data
US 2007/0282103 A1 Dec. 6, 2007

(30) Foreign Application Priority Data
Dec. 5, 2003 (GB) ................. 0328243.1

(51) Int. Cl.
C07D 487/00 (2006.01)
C07D 471/00 (2006.01)
C07D 491/00 (2006.01)

(52) U.S. Cl. ....................... 544/262; 544/255
(58) Field of Classification Search .......... None
See application file for complete search history.

(56) References Cited

U.S. PATENT DOCUMENTS

| | | | |
|---|---|---|---|
| 2,924,472 A | 2/1960 | Bush | |
| 3,182,062 A | 5/1965 | Pachter et al. | |
| 3,318,900 A | 5/1967 | Janssen | |
| 3,445,120 A | 5/1969 | Barr | |
| 4,061,459 A | 12/1977 | Parmann | |
| 4,126,689 A | 11/1978 | Sanczuk et al. | |
| 4,188,040 A | 2/1980 | Wolf et al. | |
| 4,213,619 A | 7/1980 | Arlt et al. | |
| 4,234,199 A | 11/1980 | Moncaster et al. | |
| 4,278,677 A | 7/1981 | Nedelec et al. | |
| 4,410,528 A | 10/1983 | Teranishi et al. | |
| 4,483,544 A | 11/1984 | Faerber et al. | |
| 4,641,858 A | 2/1987 | Roux | |
| 5,064,207 A | 11/1991 | Bengtsson | |
| 5,169,161 A | 12/1992 | Jones | |
| 5,297,824 A | 3/1994 | Imhof et al. | |
| 5,521,197 A | 5/1996 | Audia | |
| 5,599,028 A | 2/1997 | Neumann et al. | |
| 5,826,887 A | 10/1998 | Neumann et al. | |
| 5,988,695 A | 11/1999 | Corbett, Jr. | |
| 6,142,484 A | 11/2000 | Valls, Jr. | |
| 6,172,067 B1 | 1/2001 | Ito et al. | |
| 6,248,755 B1 | 6/2001 | Chapman et al. | |
| 6,329,381 B1 | 12/2001 | Kurimoto et al. | |
| 6,407,121 B1 | 6/2002 | Nagamine et al. | |
| 6,432,981 B1 | 8/2002 | Finke et al. | |
| 6,790,850 B1 | 9/2004 | Willis et al. | |
| 6,790,854 B2 | 9/2004 | Tsushima et al. | |
| 6,875,868 B2 | 4/2005 | Bonnert et al. | |
| 6,949,643 B2 | 9/2005 | Bonnert | |
| 6,958,343 B2 | 10/2005 | Bonnert et al. | |
| 6,958,344 B2 | 10/2005 | Bonnert et al. | |
| 7,071,193 B2 | 7/2006 | Bonnert et al. | |
| 7,169,778 B2 | 1/2007 | Denny et al. | |
| 2003/0032642 A1 | 2/2003 | Bonnert et al. | |
| 2003/0107189 A1 | 6/2003 | Bonnert et al. | |
| 2003/0119869 A1 | 6/2003 | Burrows et al. | |
| 2004/0157853 A1 | 8/2004 | Bonnert | |
| 2004/0224961 A1 | 11/2004 | Willis et al. | |
| 2005/0171345 A1 | 8/2005 | Bonnert et al. | |
| 2005/0234077 A1 | 10/2005 | Bonnert et al. | |
| 2005/0272750 A1 | 12/2005 | Brough et al. | |
| 2006/0100221 A1 | 5/2006 | Bonnert | |
| 2006/0111569 A1 | 5/2006 | Bonnert | |
| 2007/0142352 A1 | 6/2007 | Bonnert et al. | |
| 2007/0282103 A1 | 12/2007 | Butters et al. | |
| 2008/0306262 A1 | 12/2008 | Bonnert | |
| 2009/0043097 A1 | 2/2009 | Butters et al. | |

FOREIGN PATENT DOCUMENTS

| | | |
|---|---|---|
| DE | 2331223 | 1/1974 |
| DE | 41 19 767 A1 | 12/1992 |
| EP | 0 293 078 A1 | 11/1988 |
| EP | 0 447 324 A1 | 9/1991 |
| EP | 0 778 277 A1 | 6/1997 |
| EP | 1 069 124 B1 | 1/2001 |
| EP | 1 122 257 A1 | 8/2001 |
| EP | 1 348 709 B1 | 10/2003 |
| GB | 1009477 | 11/1965 |

(Continued)

OTHER PUBLICATIONS

Vippagunta, et. al., Advanced Drug Delivery Reviews; 48, (2001) 3-26.*

(Continued)

*Primary Examiner*—James O Wilson
*Assistant Examiner*—Jeffrey H Murray
(74) *Attorney, Agent, or Firm*—Fish & Richardson P.C.

(57) ABSTRACT

A method for the preparation of a compound of formula (I) or a pharmaceutically acceptable salt or solvate thereof; from a compound of the formula: (IV); wherein L represents a leaving group.

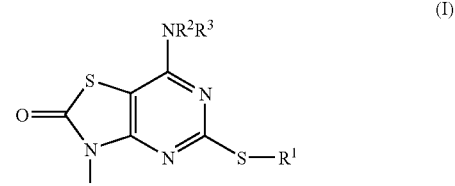

(I)

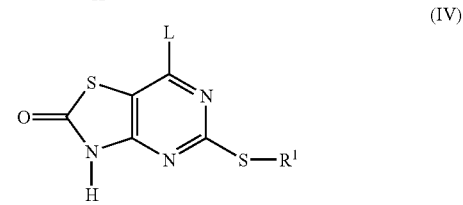

(IV)

7 Claims, No Drawings

FOREIGN PATENT DOCUMENTS

| | | |
|---|---|---|
| GB | 2359079 A | 8/2001 |
| JP | 51-88994 | 7/1993 |
| WO | WO 97/22596 | 6/1997 |
| WO | WO 97/30035 | 8/1997 |
| WO | WO 97/32856 | 9/1997 |
| WO | WO 97/40035 | 10/1997 |
| WO | WO 98/08847 | 3/1998 |
| WO | WO 98/13354 | 4/1998 |
| WO | WO 98/25617 | 6/1998 |
| WO | WO 99/02166 | 1/1999 |
| WO | WO 99/04794 | 2/1999 |
| WO | WO 99/17773 | 4/1999 |
| WO | WO 99/36421 | 7/1999 |
| WO | WO 99/51608 | 10/1999 |
| WO | WO 00/08013 | 2/2000 |
| WO | WO 00/09511 | 2/2000 |
| WO | WO 00/38680 | 7/2000 |
| WO | WO 00/39129 | 7/2000 |
| WO | WO 00/40529 | 7/2000 |
| WO | WO 00/41669 | 7/2000 |
| WO | WO 00/45800 | 8/2000 |
| WO | WO 00/59502 | 10/2000 |
| WO | WO 00/76514 | 12/2000 |
| WO | WO 01/19825 | 3/2001 |
| WO | WO 01/25200 | 4/2001 |
| WO | WO 01/25242 | 4/2001 |
| WO | WO01/025242 * | 4/2001 |
| WO | WO 01/58902 | 8/2001 |
| WO | WO 01/58906 | 8/2001 |
| WO | WO 01/66525 | 9/2001 |
| WO | WO 01/92224 | 12/2001 |
| WO | WO 02/04434 | 1/2002 |
| WO | WO 02/08213 | 1/2002 |
| WO | WO02083693 * | 10/2002 |
| WO | WO 03/024966 | 3/2003 |
| WO | WO 2004/026835 | 1/2004 |
| WO | WO 2004/026880 | 4/2004 |
| WO | WO 2005/033115 | 4/2005 |
| WO | WO 2005/056563 | 6/2005 |
| WO | WO 2005/082865 | 9/2005 |
| WO | WO 2006/064228 | 6/2006 |

OTHER PUBLICATIONS

Ahmed et al., "Novel synthesis of 1-aryl-9-alky1-2,3,3a,4,9,9a-hexahydro-1H-pyrrolo[2,3-b]quinoxalines by lithium aluminum hydride reduction of N-phenyl-1-benzimidazolylsuccinimides", CAPLUS 79:92106 (1973).

Baly et al., "Biological Assays for C-X-C Chemokines", *Methods in Enzymology* 287:69-88 (1997).

Baxter et al., "Hit-to-Lead Studies: The Discovery of Potent, Orally Bioavailable Thiazolopyrimidine CXCR2 Receptor Antagonists", *Bioorg. Med. Chem. Lett.* 16(4):90-963 (2006).

Berge et al., "Pharmaceutical Salts", *J Pharm. Sci.* 66:1-19 (1977).

Bodor et al., "Chemical Approaches to Drug Delivery", in: *Encyclopedia of Controlled Drug Delivery* (1999 ed.), pp. 285-298.

CAPLUS, Accession No. 2000:76301, Document No. 132:98128, "Antiinflammatory and analgesic capsules containing betamethasone, vitamin B6, dihydrochlorothiazide and triamterene".

Chemcats, Accession No. 2001:1442861, "4, 7-Pteridinediamine, 9-phenyl-2-[(phenylmethyl)thio]-," CAS Registry 343347-55-7 (Jul. 1, 2001).

Chemical Abstracts, vol. 54, No. 10, May 1960, Abstract No. 9933f, C. Wayne Noell and Roland K. Robins, "Potential Purine Antagonists XVII. Synthesis of 2-methyl and 2-methylthio-6, 8-disubstituted purines", see formula III when R-SMe, R1=C1, R2=OH Cohen et al., "Cytokine function: A study in biologic diversity", CAPLUS 125:31527 (1996).

Cowley et al., "Preparation of 1-(3-phenyloxypropyl)piperdine derivatives as opioid receptor ligands", CAPLUS 138:39189 (2002).

Faubl, "Preparation of 5-Tetrazolyl Groups from Carboxylic Acids. A Sequence Amenable to Sensitive Substrates", *Tetrahedron Letters* 6:491-494 (1979).

Finke et al., "Preparation of piperidinylmethylcyclopentanes as modulators of CCR-5 and/or CCR-3 chemokine receptors", CAPLUS 134:56576 (2000) CAS Listing, 77 answers.

Fukuda et al., "Preparation of benzotriazole derivatives as cardiovascular agents and antipsychotics", CAPLUS 123:340149 (1995).

Gavezzotti, "Are Crystal Structures Predictable?", *Acc. Chem. Res.* 27:309-314 (1994).

Gewald et al., "New Synthesis of Substituted 4-Amino-quinazolines and Their Heteroanaloga", *J. prakt. Chem.* 338:206-213 (1996).

Grant, "University of Minnesota—Twin Cities Campus College of Pharmacy, Annual Report", [online] 1999, [retrieve on Feb. 13, 2003]. Retrieved from the internet, http://www.msi.umn.edu/general/Reports/ar99/departments/pharmacy.html.

Grohe et al., "Cycloacylation of Enamines, I.—Synthesis of 2-Thiazolone Derivatives", *Liebigs Ann. Chem.* 1018-1024 (1973).

Kiriasis et al., "Synthesis and Properties of New Pteridine Nucleosides", *Dev. Biochem.* 4:49-53 (1978).

Lee et al., "Characterization of Two High Affinity Human Interleukin-8 Receptors", *J. Biol. Chem.* 267:16283-16287 (1992).

McNaught et al., "IUPAC Compendium of Chemical Terminology, $2^{nd}$ Ed" (1997).

Merritt et al., "Use of fluo-3 to measure cytosolic $Ca^{2+}$ in platelets and neutrophils: Loading cells with the dye, calibration of traces, measurements in the presence of plasma, and buffering of cytosolic $Ca^{2+}$", *Biochem. J.* 269:513-519 (1990).

Murdoch and Finn, "Chemokine receptors and their role in inflammation and infectious diseases", *Blood* 95:3032 (3043 (2000).

Nagahara et al., "Thiazolo[4,5-*d*]pyrimidine Nucleosides. The Synthesis of Certain 3-β-D-Ribofuranosylthiazolo(4,5-*d*]pyrimidines as Potential Immunotherapeutic Agents", *J. Med. Chem.* 33:407-415 (1990).

Ott et al., "4-amino-7, 8-dihydro-2-(methylmercapto)-8-β, -D-ribofuranosylpteridin-7-One. Modified Fusion Reaction with trimethylsilylated Pteridine Derivatives", *Nucl. Acid. Chem.* 2:735-739 (1978).

Ott et al., "Zur Synthese des 4-Amino-7-oxo-7, 8-dihydropteridin-N-8-β-D-ribofuranosids—ein strukturanaloges Nucleosid des Adenosins", *Chem.Ber.* 107:339-361 (1974).

Pachter and Nemeth, "Pteridines. I. Synthesis of Some 6-Alkyl-7-aminopteridines from Nitrosopyrimidines", *J. Org. Chem.* 28:1187-1191 (1963).

Patent Abstracts of Japan, abstract of JP-5-202047 A (Chugai Pharmaceut. Co. Ltd.) Aug. 10, 1993.

Power et al., "Differential Histopathology and Chemokine Gene Expression in Lung Tissues following Respiratory Syncytial Virus (RSV) Challenge of Formalin-Inactivated RSV- or BBG2Na-Immunized Mice", *J. Virol.* 75:12421-12430 (2001).

Sato et al., "Psychotropic Agents. 3.4-(4-Substituted piperidinyl)-1-(4-flurophenyl)-1-butanones with Potent Neuroleptic Activity," *Journal of Medicinal Chemistry* 21(11):1116-1120 (1978).

Souillac et al., "Characterization of Delivery Systems, Differential Scanning Calorimetry", in: *Encyclopedia of Controlled Drug Delivery* (1999 ed.), pp. 212-227.

Spickett and Timmis, "The Synthesis of Compounds with Potential Anti-folic Acid Activity. Part I. 7-Amino- and 7-Hydroxypteridines", *J. Chem, Soc.* pp. 2887-2895 (1954).

Taylor et al., "Molecular Determinants for Recognition of RU 24969 Analogs at Central 5-Hydroxytryptamine Recognition Sites: Use of a Bilinear Function and Substituent Volumes to Describe Steric Fit," *Molecular Pharmacology* 32:42-53 (1988).

Teranishi et al., "Piperidine derivatives and pharmaceutical compositions containing them", CAPLUS 95:132947 (1981).

Trivedi et al., "Section IV. Immunology, Endocrinology and Metabolic Diseases", *Annual Reports in Medicinal Chemistry* 35:191-200 (2000).

Vandenberk et al., "1-(Benzazolylalkyl)piperidines and their salts with acids", CAPLUS 87:23274 (1977).

Vartanyan et al., "Synthesis and biological activity of 1-substituted benzimidazole and benztriazole derivatives", CAPLUS 98:4503 (1983).

Weinstock et al., "Pteridines. XII. Structure-Activity Relationships of Some Pteridine Diuretics", *J. Med. Chem.* 11(3):573-579 (1968).

West, "Solid State Chemistry and its applications", Wiley, New York, pp. 358 & 365 (1988).

Wu et al., "Synthesis of Furanonaphthoquinones with Hydroxyamino Side Chains", *J. Nat. Prod.* 62:963-968 (1999).

Traves et al., "Specific CXC but not CC chemokines cause elevated monocyte migration in COPD: a role for $CXCR^{2}$", *Journal of Leukocyte Biology* 76:441-450 (2004).

Sato et al., "Psychotropic agents. 3.4-(4-Substituted piperidinyl)-1-(4-fluropheny1)-1-butanones with potent neuroleptic activity", CAPLUS, AN 1978:608915; DN 89:208915.

* cited by examiner

PROCESS FOR THE PREPARATION OF THIAZOLOPYRIMIDINES

CROSS-REFERENCE TO RELATED APPLICATIONS

This application is a national phase application under 35 U.S.C. §371 of PCT International Application No. PCT/GB2004/005072, filed Dec. 2, 2004, which claims priority to Swedish Application Ser. No. 0328243.1, filed Dec. 5, 2003.

METHODS

The present invention relates to methods for preparing thiazolopyrimidine compounds, intermediate compounds used in such methods, thiazolopyrimidine compounds so prepared and their use in therapy.

In our published PCT patent application WO-01/25242 we describe pharmaceutically active compounds of the general formula I

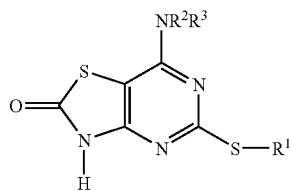

(I)

and pharmaceutically acceptable salts and solvates thereof, and methods for their preparation. Such methods include treatment of a compound of formula

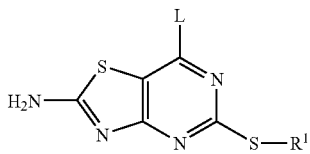

where L is a leaving group such as chlorine, with an amine $HNR^2R^3$.

We have now devised an advantageous process for preparing compounds of the formula I. This novel process involves protection of the thiazole nitrogen atom and gives an improved yield of final product when compared with the prior art method described in WO-01/25242. By way of example for a compound of the above formula we have achieved displacement of a chlorine leaving group by a group $NR^2R^3$ and subsequent conversion of the 2-amino group to a carbonyl group, with about 40% overall yield. In contrast we have achieved about 70% overall yield for the same product starting from a compound of formula IV as set out hereinafter and wherein the leaving group L is chlorine.

Therefore in a first aspect of the invention we provide a method for the preparation of a compound of formula (I) or a pharmaceutically acceptable salt or solvate thereof:

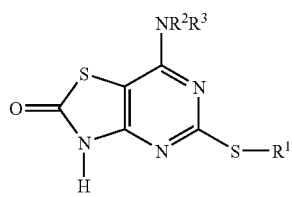

(I)

in which
$R^1$ represents a $C_3$-$C_7$ carbocyclic, $C_1$-$C_8$ alkyl, $C_2$-$C_6$ alkenyl or $C_2$-$C_6$ alkynyl group, each of the groups being optionally substituted by one or more substituent groups independently selected from halogen atoms, —$OR^4$, —$NR^5R^6$, —$CONR^5R^6$, —$COOR^7$, —$NR^8COR^9$, —$SR^{10}$, —$SO_2R^{10}$, —$SO_2NR^5R^6$, —$NR^8SO_2R^9$ or an aryl or heteroaryl group, both of which may be optionally substituted by one or more substituents independently selected from halogen atoms, cyano, nitro, —$OR^4$, —$NR^5R^6$, —$CONR^5R^6$, —$COOR^7$, —$NR^8COR^9$, —$SR^{10}$, —$SO_2R^{10}$, —$SO_2NR^5R^6$, —$NR^8SO_2R^9$, $C_1$-$C_6$ alkyl or trifluoromethyl groups;

$R^2$ and $R^3$ each independently represent a hydrogen atom, or a $C_3$-$C_7$ carbocyclic, $C_1$-$C_8$ alkyl, $C_2$-$C_6$ alkenyl or $C_2$-$C_6$ alkynyl group, the latter four groups may be optionally substituted by one or more substituent groups independently selected from:

(a) halogen atoms, —$OR^4$, —$NR^5R^6$, —$CONR^5R^6$, —$COOR^7$, —$NR^8COR^9$, —$SR^{10}$, —$SO_2R^{10}$, —$SO_2NR^5R^6$, —$NR^8SO_2R^9$;

(b) a 3-8 membered ring optionally containing one or more atoms selected from O, S, $NR^8$ and itself optionally substituted by $C_1$-$C_3$-alkyl or halogen; or (c) an aryl group or heteroaryl group each of which may be optionally substituted by one or more substituents independently selected from halogen atoms, cyano, nitro, —$OR^4$, —$NR^5R^6$, —$CONR^5R^6$, —$NR^8COR^9$, —$SO_2NR^5R^6$, —$NR^8SO_2R^9$, $C_1$-$C_6$ alkyl and trifluoromethyl groups;

$R^4$ represents hydrogen, $C_1$-$C_6$ alkyl or a phenyl group the latter two of which may be optionally substituted by one or more substituent groups independently selected from halogen atoms, phenyl, —$OR^{11}$ and —$NR^{12}R^{13}$.

$R^5$ and $R^6$ independently represent a hydrogen atom or a $C_1$-$C_6$ alkyl or phenyl group the latter two of which may be optionally substituted by one or more substituent groups independently selected from halogen atoms, phenyl, —$OR^{14}$ and —$NR^{15}R^{16}$, —$CONR^{15}R^{16}$, —$NR^{15}COR^{16}$— $SONR^{15}R^{16}$, $NR^{15}SO_2R^{16}$ or $R^5$ and $R^6$ together with the nitrogen atom to which they are attached form a 4- to 7-membered saturated heterocyclic ring system optionally containing a further heteroatom selected from oxygen and nitrogen atoms, which ring system may be optionally substituted by one or more substituent groups independently selected from phenyl, —$OR^{14}$, —$COOR^{14}$, —$NR^{15}R^{16}$, —$CONR^{15}R^{16}$, —$NR^5COR^{16}$, —$SONR^{15}R^{16}$, $NR^{15}SO_2R^{16}$ or $C_1$-$C_6$ alkyl, itself optionally substituted by one or more substituents independently selected from halogen atoms and —$NR^{15}R^{16}$ and —$OR^{17}$ groups;

$R^{10}$ represents a hydrogen atom or a $C_1$-$C_6$-alkyl or a phenyl group, the latter two of which may be optionally substituted by one or more substituent groups independently selected from halogen atoms, phenyl, —$OR^{17}$ and —$NR^{15}R^{16}$; and each of $R^7$, $R^8$, $R^9$, $R^{11}$, $R^{12}$, $R^{13}$, $R^{14}$, $R^{15}$, $R^{16}$, $R^{17}$ independently represents a hydrogen atom or a $C_1$-$C_6$ alkyl, or a phenyl group;

which method comprises contacting

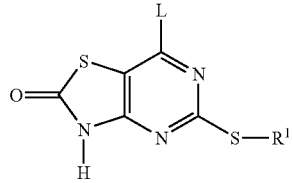

IV wherein L is a leaving group with a thiazole nitrogen protecting group reagent under appropriate reaction conditions to form a compound of the formula

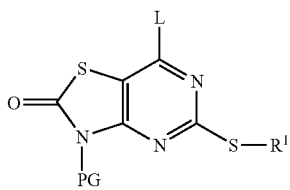

III wherein PG is a protecting group, reacting the compound of formula III with an amine of formula $HNR^2R^3$ to form a compound of formula

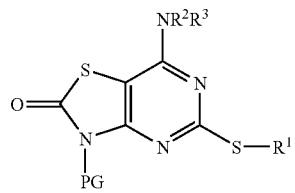

II and deprotection of the compound of formula II to give a compound of the formula I, and simultaneous or sequential conversion to a pharmaceutically acceptable salt or solvate thereof.

Convenient leaving groups will be apparent to the chemist of ordinary skill, such as disclosed in 'Advanced Organic Chemistry', $4^{th}$, edition, J. March, Wiley-Interscience (1992). Such groups will include halogen atoms such as chlorine or bromine. Chlorine is a preferred leaving group for use in the invention.

Additional protection may be provided for the amine of formula $HNR^2R^3$ for example where $R^2$ and/or $R^3$ comprises a hydroxy or amino group. By way of non-limiting example we refer to Example 3(d) where a particular diol is introduced and protected via the compound (2,2,5-trimethyl-1,3-dioxan-5-yl)amine.

Convenient protecting groups will be apparent to the chemist of ordinary skill. It will be appreciated that the more stable the resulting product upon protection the likelihood of increased difficulty in removing the protecting group afterwards. Additionally, some resulting products upon protection may not be sufficiently stable to isolation by standard laboratory methods. The protection and deprotection of functional groups is fully described in 'Protective Groups in Organic Synthesis', 2nd edition, T. W. Greene & P. G. M. Wuts, Wiley-Interscience (1991).

Examples of suitable protecting groups for the given transformations, to provide compounds of formula I, involving removal under appropriate hydrolytic conditions are [with suitable protecting group agents indicated in square brackets] methoxymethyl [chloromethyl methyl ether], and particularly ethoxymethyl [chloromethyl ethyl ether or diethoxymethane], benzyloxymethyl [benzyl chloromethyl ether], pivaloyloxymethyl [chloromethyl pivalate], 2-(trimethylsilyl)ethoxymethyl [2-(trimethylsilyl)ethoxymethyl chloride], 1-(ethoxy)ethyl [ethyl vinyl ether] and 2-tetrahydropyranyl [3,4-dihydro-(2H)-pyran]. Each individual protecting group listed above and its use represents a particular independent aspect of the invention. Base-assisted removal of the 2-(phenylsulfonyl)ethyl [phenyl vinyl sulfone] protecting group under non-aqueous conditions is a suitable method for achieving these transformations.

The approach is also suited to catalytic reduction methods for removal of appropriate protecting groups. Such protecting groups include benzyl, diphenylmethyl, triphenylmethyl and benzyloxymethyl. Allyl as a protecting group can be removed under metal-assisted conditions and 4-methoxybenzyl, 2,4-dimethoxybenzyl and di(4-methoxyphenyl)methyl can be removed under oxidative conditions. Acyl, benzoyl, pyrrolidinylmethyl and urea-type protecting groups are other examples that can be removed under appropriate hydrolytic conditions. Representative chloroformate reagents do not yield a carbamate protecting group, for example a benzylchloroformate reagent is found to yield a benzyl protecting group.

In the context of the present specification, unless otherwise indicated, an alkyl or alkenyl group or an alkyl or alkenyl moiety in a substituent group may be linear or branched. Aryl groups include phenyl and naphthyl. Heteroaryl groups include 5- or 6-membered aromatic rings containing one or more heteroatoms selected from N, S, and O. Examples include pyridine, pyrimidine, thiazole, oxazole, pyrazole, imidazole, furan.

Certain compounds of formula (I) are capable of existing in stereoisomeric forms. It will be understood that the methods of the invention may be used with all geometric and optical isomers of the compounds of formula (I) and mixtures thereof including racemates. The scientist of ordinary skill will be able to select appropriate intermediate compounds to introduce the appropriate stereochemistry for —$NR^2R^3$ and $R^1$ (if appropriate).

Particular compounds of formula (I) are those in which $R^1$ represents an optionally substituted benzyl group. More particularly $R^1$ represents benzyl or benzyl substituted by one or more $C_1$-$C_6$ alkyl, $C_1$-$C_6$ alkoxy or halogen atoms.

When $R^2$ and $R^3$ represent a group substituted by one or more 3-8 membered rings optionally containing one or more atoms selected from O, S or $NR^8$, examples of such groups include piperidine, pyrrolidine, piperazine and morpholine.

Conveniently one of $R^2$ or $R^3$ is hydrogen and the other is $C_1$-$C_8$ alkyl substituted by hydroxy and one or more methyl or ethyl groups. More conveniently one of $R^2$ or $R^3$ is hydrogen and the other is $CH(CH_3)CH_2OH$, $CH(Et)CH_2OH$, $C(CH_3)_2CH_2OH$ or $CH(CH_2OH)_2$. When one of $R^2$ or $R^3$ is hydrogen and the other is $CH(CH_3)CH_2OH$ or $CH(Et)CH_2OH$ the resulting compounds of formula (I) are particularly in the form of the (R) isomer.

Particular compounds of the formula I for use in the method of the invention include those wherein $R^1$ represents a (2,3-difluorophenyl)methyl group and $R^2$ and $R^3$ together represent a $C_{1-8}$ alkyl group optionally substituted by one or more substituent groups independently selected from —$OR^4$ wherein $R^4$ represents hydrogen or a $C_{1-6}$ alkyl group.

Further particular compounds of the formula I include compounds of the formula Ia Ia

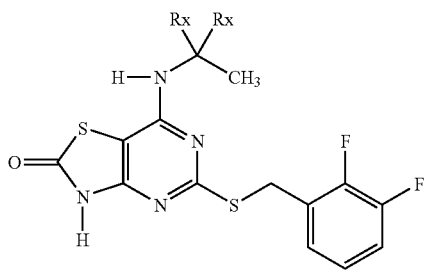

wherein each $R^x$ is independently selected from hydrogen, a $C_{1-4}$ alkyl group optionally substituted by hydroxy, ammo, —O—$C_{1-4}$ alkyl, —S—$C_{1-4}$ alkyl, —N—$C_{1-4}$ alkyl, —NHSO$_2$R, or —CONR$_2$ and provided that both $R^x$ are not hydrogen or amino.

More particular compounds of the invention are wherein each $R^x$ is independently selected from hydrogen and hydroxymethyl, provided that both $R^x$ are not hydrogen.

The invention also provides novel salts of the above compounds namely the potassium salt of the compound wherein one $R^x$ is hydrogen and the other is hydroxymethyl (cf. Example 2) and both the sodium and potassium salts of the compound wherein both $R^x$ are hydroxymethyl (Examples 3 and 4).

Compounds of the formula II are novel and represent a further aspect of the invention.

Preparation of a Compound of the Formula I Via Deprotection of a Compound of the formula II is novel and represents a further aspect of the invention.

Compounds of the formula III are novel and represent a further aspect of the invention.

Preparation of a Compound of the Formula Ii Via Reaction of a Compound of the formula III with an amine of formula HNR$_2$R$_3$ is novel and represents a further aspect of the invention.

Compounds of the formula IV are novel (except for 7-chloro-5-[[(2,3-difluorophenyl)methyl]thio]thiazolo[4,5-d]pyrimidin-2-(3H)-one) and represent a further aspect of the invention. They are conveniently prepared by reaction of a compound of formula

V

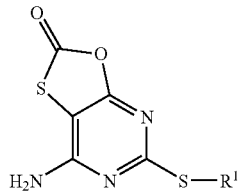

with a reagent providing a leaving group L.

Such reaction represents a further independent aspect of this invention.

Compounds of the formula V are novel and represent a further aspect of the invention. They are conveniently prepared by reaction of a compound of formula

VI

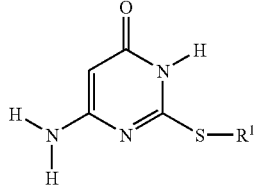

with a halocarbonylsulfenylhalide. Convenient halogen atoms are independently selected from chlorine and bromine, chlorine is a preferred halogen atom and chlorocarbonylsulfenylchloride is a preferred reagent.

Such reaction represents a further independent aspect of this invention.

Compounds of formula VI are novel and represent a further, independent aspect of the invention, they are conveniently prepared by reaction of a compound of formula

VII

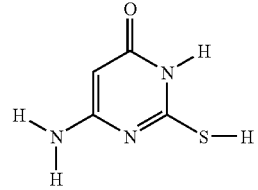

with a compound of formula L-R$^1$, wherein L is a leaving group and R$^1$ is as hereinbefore defined.

Such reaction is known for reaction of the compound of formula VII with a compound L-R$^1$ wherein L is bromine and R$^1$ is (2,3-difluorophenyl)methyl, this is disclosed in our WO-03/24966.

The compound of formula VII is conveniently provided as the monohydrate (cf. Example 1 (a)) and is commercially available, for example from Aldrich, Acros or Lancaster.

In a further aspect of the invention we provide the preparation of a compound of formula I from a compound of Formula V, via compounds of Formula IV, III, II, using methods as set out hereinbefore.

In a further aspect of the invention we provide the preparation of a compound of formula I from a compound of Formula VI, via compounds of Formula V, IV, III, II, using methods as set out hereinbefore.

In a further aspect of the invention we provide the preparation of a compound of formula I from a compound of Formula VII, via compounds of Formula VI, V, IV, III, II, using methods as set out hereinbefore.

The invention will now be illustrated but not limited by the following Examples:

EXAMPLE 1

5-[[(2,3-difluorolphenyl)methyl]thio]-7-[[(1R)-2-hydroxy-1-methylethyl]amino]thiazolo[4,5-d]pyrimidin-2(3H)-one (a) 6-amino-2-[[(2,3-difluorophenyl)methyl]thio]-4-pyrimidinol

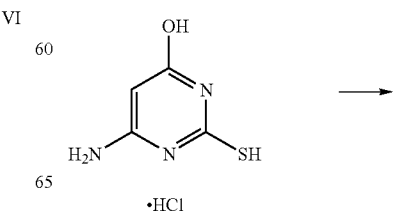

•HCl

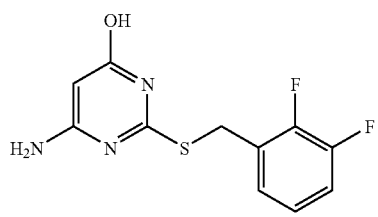

To a stirred suspension of 4-amino-6-hydroxy-2-mercaptopyrimidine monohydrate (67.7 g) in a mixture of water (920 ml) and tetrahydrofuran (300 ml) was added aqueous sodium hydroxide solution (46-48% w/w; 24 ml) followed by water (40 ml). The resulting hazy, pale yellow solution was cooled to 20° C. before adding 2,3-difluorobenzyl bromide (83.0 g) uniformly over 25 minutes, to yield a white precipitate. The mixture was stirred at ambient temperature for 3.5 hours, the product collected and washed twice with a mixture of water (68 ml) and tetrahydrofuran (24 ml), to afford the title compound as a white solid (101.89 g).

$^1$H NMR: δ (DMSO-d6) 11.45 (1H, br.s), 7.44 (1H, t), 7.34 (1H, m), 7.15 (1H, m), 6.58 (2H, br.s), 5.01 (1H, s), 4.39 (2H, s).

(b) 7-amino-5-[[(2,3-difluorophenyl)methyl]thio][1,3]oxathiolo[5,4-d]pyrimidin-2-one

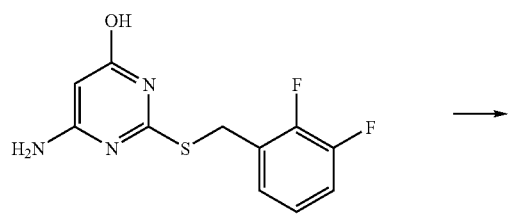

To a stirred suspension of 6-amino-2-[[(2,3-difluorophenyl)methyl]thio]-4-pyrimidinol (9.58 g) in tetrahydrofuran (96 ml) was added chlorocarbonylsulfenyl chloride (4.89 g) over 7 minutes, followed by tetrahydrofuran (2 ml). The reaction mixture was stirred for 40 minutes and the resulting precipitate collected by filtration, washing twice with tetrahydrofuran (19 ml), to afford the title compound as a pale yellow solid (11.31 g).

$^1$H NMR: δ (DMSO-d6) 7.89 (1H, br.s), 7.45 (1H, t), 7.34 (1H, m), 7.16 (1H, m), 5.82 (1H, br.s), 4.39 (2H, s).

(c) 7-chloro-5-[[(2,3-difluorophenyl)methyl]thio]thiazolo[4,5-d]pyrimidin-2-(3H)-one

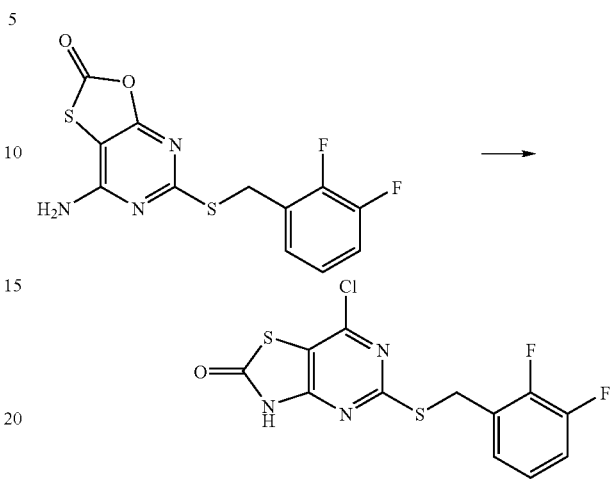

To a stirred suspension of 7-amino-5-[[(2,3-difluorophenyl)methyl]thio][1,3]oxathiolo[5,4-d]pyrimidin-2-one (5.03 g) and benzyltrimethylammonium chloride (2.58 g) in acetonitrile (25 ml) at 50° C., was first added N,N-diethylaniline (2.46 g) followed by acetonitrile (5 ml), and then phosphorus oxychloride (7.41 g) followed by acetonitrile (5 ml). The reaction mixture was heated to reflux and maintained at this temperature for 36 hours, before cooling to ambient temperature and adding to water (25 ml) at 50° C. with stirring over 30 minutes. An additional acetonitrile (5 ml) rinse of the reaction vessel was added to the drown-out mixture, before heating to 75° C. and slowly cooling to 25° C. at <0.5° C./min. The resulting mixture was held at 25° C. for 30 minutes and then collected by filtration, washing four times with water (25 ml), to afford the title compound as an off-white solid (3.5 g).

$^1$H NMR: δ (DMSO-d6) 7.45 (1H, t), 7.38 (1H, m), 7.22 (1H, m), 4.50 (2H, s), 3.43 (1H, br.s).

(d) 5-[[(2,3-difluorophenyl)methyl]thio]-7-[[(1R)-2-hydroxy-1-methylethyl]amino]-3-(tetrahydro-2H-pyran-2-yl)thiazolo[4,5-d]pyrimidin-2-(3H)-one

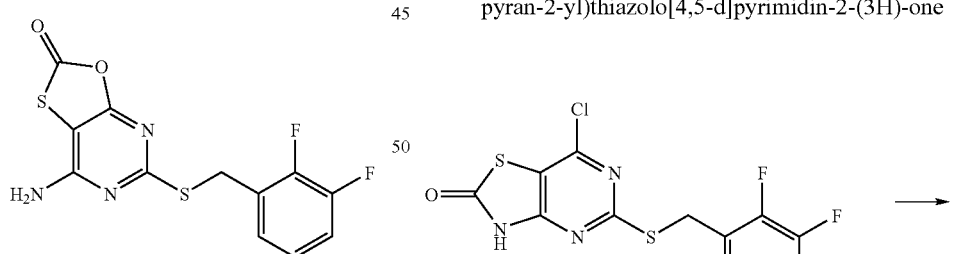

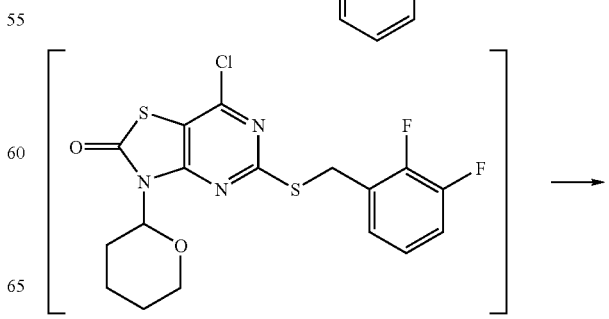

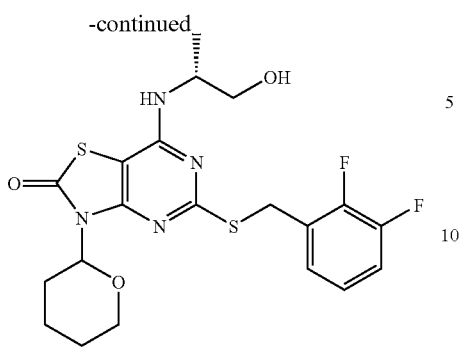

(i) To a stirred suspension of 7-chloro-5-[[(2,3-difluorophenyl)methyl]thio]thiazolo[4,5-d]pyrimidin-2-(3H)-one (5 g) and p-toluenesulfonic acid (29.4 mg) in toluene (40 ml) at 60° C. was added 3,4-dihydro-2H-pyran (1.83 g) over 1 hour. The reaction mixture was held at 60° C. for 2 hours and then cooled at 0.5° C./min to ambient temperature. Saturated aqueous sodium bicarbonate solution (20 ml) was first added to the reaction mixture, before stirring for 1 hour. The settled phases were separated and the organic solution further treated with saturated brine (20 ml). The brine phase was removed and toluene (2 ml) added to the remaining organic phase to give a clear orange solution of 7-chloro-5-[[(2,3-difluorophenyl)methyl]thio]-3-(tetrahydro-2H-pyran-2-yl)thiazolo[4,5-d]pyrimidin-2-(3H)-one. (44.5 ml).

(ii) To a portion of the clear orange solution (10 ml) was added tetrahydrofuran (5 ml), sodium carbonate (0.70 g) and (D)-alaninol (0.49 g). The stirred reaction mixture was heated to 60° C. for 1.5 hours and then further heated to 65° C. for 24 hours. Water (10 ml) was added to the reaction mixture at 60° C. and stirring continued for 1 hour. The settled aqueous phase was removed and cyclohexane (15 ml) added to the stirred reaction mixture over 1 hour at 60° C., during which time the product crystallised. The resulting mixture was stirred at 60° C. for a further 2 hours, cooled to ambient temperature at 0.25° C./min and then cooled to 0-5° C. The crystallised product was isolated, washed twice with toluene (3 ml), to afford the title compound as an off-white solid (1.15 g).

$^1$H NMR: δ (DMSO-d6) 7.50 (1H, br.s), 7.41 (1H, t), 7.33 (1H, m), 7.15 (1H, m), 5.54 (1H, d), 4.76 (1H, br.s), 4.44 (2H, s), 4.22 (1H, br.m), 4.00 (1H, d), 3.56 (1H, m), 3.43 (1H, m), 3.34 (1H, m), 2.71 (1H, m), 1.90 (1H, br.d), 1.62 (2H, br.d), 1.48 (2H, br.m), 1.10 (3H, d).

(e) 5-[[(2,3-difluorophenyl)methyl]thio]-7-[[(1R)-2-hydroxy-1-methylethyl]amino]thiazolo[4,5-d]pyrimidin-2-(3H)-one

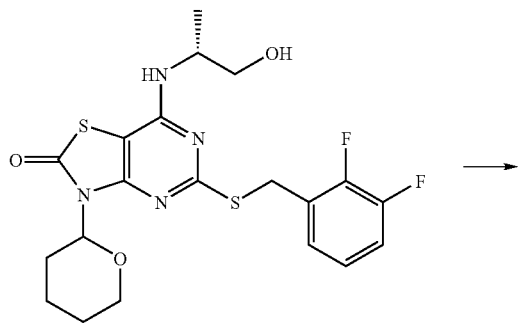

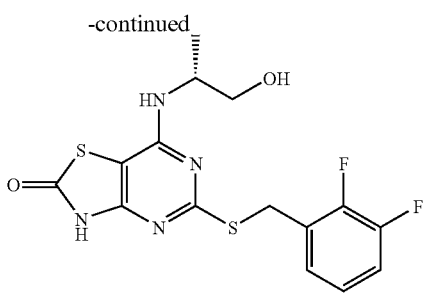

To a stirred solution of 5-[[(2,3-difluorophenyl)methyl]thio]-7-[[(1R)-2-hydroxy-1-methylethyl]amino]-3-(tetrahydro-2H-pyran-2-yl)thiazolo[4,5-d]pyrimidin-2-(3H)-one (10.0 g) in acetonitrile (200 ml), water (36 ml) and tetrahydrofuran (30 ml) at 65° C. was added 1M hydrochloric acid (23.25 ml) over 3 hours. The product crystallised during the addition time. The mixture was cooled to 25° C. and the product collected by filtration, washing firstly with water (30 ml) then acetonitrile (30 ml), to afford the title compound as an off-white solid (7.79 g).

$^1$H NMR: δ (DMSO-d6) 12.41 (1H, br.s), 7.35 (3H, m), 7.15 (1H, m), 4.73 (1H, m), 4.40 (2H, m), 4.21 (1H, br.m), 3.44 (1H, m), 3.37 (1H, m), 1.09 (3H, d).

EXAMPLE 2

5-[[(2,3-difluorophenyl)methyl]thio]-7-[[(1R)-2-hydroxy-1-methylethyl]amino]thiazolo[4,5-d]pyrimidin-2(3H)-one, potassium salt (a) 5-[[(2,3-difluorophenyl)methyl]thio]-7-[[(1R)-2-hydroxy-1-methylethyl]amino]-3-[2-(phenylsulfonyl)ethyl]thiazolo[4,5-d]pyrimidin-2-(3H)-one

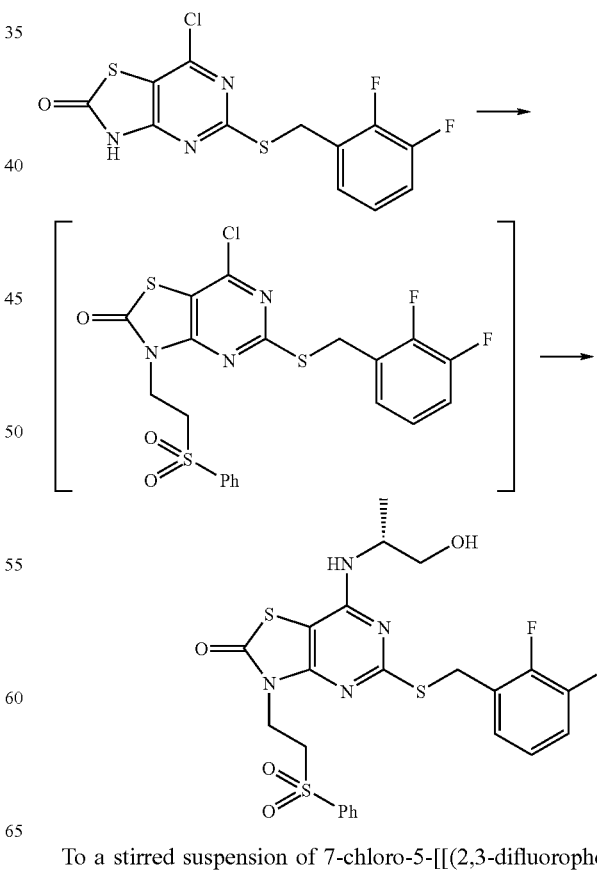

To a stirred suspension of 7-chloro-5-[[(2,3-difluorophenyl)methyl]thio]thiazolo[4,5-d]pyrimidin-2-(3l)-one (31.62 g), as prepared in Example 1 (c) above, in butyronitrile (150 ml) at room temperature was added diisopropylethylamine (16 ml, 1.0 eq), forming a solution. A butyronitrile line wash was applied (10 ml). Phenylvinylsulfone (20 g, 1.3 eq) was dissolved in butyronitrile (80 ml) in a separate flask and this solution was added to the vessel, followed by a line wash with butyronitrile (70 ml). The orange solution was heated to an internal temperature of 100° C. After 18 hours HPLC showed almost complete consumption of the starting material (3.36% 7-chloro-5-[[(2,3-difluorophenyl)methyl]thio]thiazolo[4,5-d]pyrimidin-2-(3H)-one remained)*. At this point further diisopropylethylamine (16 ml, 1.0 eq) was added to the mixture at 50° C., followed by a small line wash of butyronitrile (5 ml). D-alaninol (9.25 mLs, 1.3 eq) was added, followed by a line wash of butyronitrile (5 ml). After 6.5 hrs HPLC showed almost complete conversion of the reaction intermediate (2.52% 7-chloro-5-[[(2,3-difluorophenyl)methyl]thio]-3-[2-(phenylsulfonyl)ethyl]thiazolo[4,5-a]pyrimidin-2-(3H)-one remained). The reaction was allowed to cool from 100 to 50° C. over 6.5 hrs and held at 50° C. under nitrogen for 64 hrs. In order to get a homogeneous sample the reaction was re-heated to 100° C. (1.19% 7-chloro-5-[[(2,3-difluorophenyl)methyl]thio]-3-[2-(phenylsulfonyl)ethyl]thiazolo[4,5-d]pyrimidin-2-(3H)-one present by HPLC). The reaction was cooled from 100 to 50° C. over 1 hr and water (200 mLs) was added. A precipitate was observed. The mixture was cooled from 50° C. to 20° C. over 2 hrs. The precipitate was 'aged' at 20° C. for 1 hr and collected by filtration. The 'cake' was washed with 1:1 water/butyronitrile (70 ml) twice, then with butyronitrile (35 ml). The solid was then dried on the filter for 30 mins, collected and dried in a vacuum oven overnight at 50° C. A pale yellow solid 5-[[(2,3-difluorophenyl)methyl]thio]-7-[[(1R)-2-hydroxy-1-methylethyl]amino]-3-[2-(phenylsulfonyl)ethyl]thiazolo[4,5-d]pyrimidin-2-(3H)-one was obtained with 88% yield (44.33 g, HPLC area=98.75%).

¹H NMR: δ (DMSO-d6) 1.09 (d, 3H), 1.25 (m, 1H), 3.37 (dquin, 2H), 3.80 (t, 2H), 4.13 (t, 2H), 4.20 (m, 1H), 4.39 (s, 2H), 4.75 (t, 1H), 7.15 (m, 1H), 7.33 (m, 2H), 7.46 (d, 1H), 7.55 (t, 2H), 7.66 (t, 1H), 7.82 (d, 2H).

(b) Isolation of Intermediate 7-chloro-5-[[(2,3-difluorophenyl)methyl]thio]-3-[2-(phenylsulfonyl)ethyl]thiazolo[4,5-d]pyrimidin-2-(3H)-one This may be achieved by following the process as outlined in (a) above but adding water to mixture at 50° C. (at point *). The mixture is then cooled to room temperature producing a precipitate which is isolated by filtration.

¹H NMR: δ (DMSO-d6) 3.86 (t, 2H), 4.21 (t, 2H), 4.49 (s, 2H), 7.20 (m, 1H), 7.37 (m, 2H), 7.55 (t, 2H), 7.65 (t, 1H), 7.83 (d, 2H).

(c) Preparation of 5-[[(2,3-difluorophenyl)methyl]thio]-7-[[(1R)-2-hydroxy-1-methylethyl]amino]thiazolo[4,5-d]pyrimidin-2(3H)-one, potassium salt

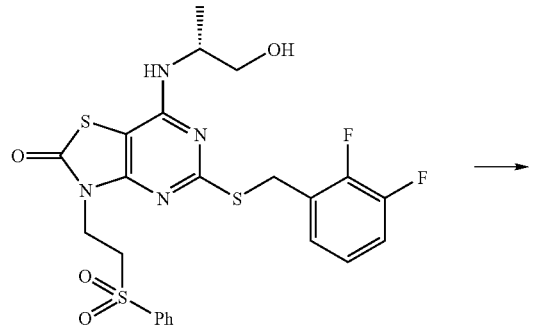

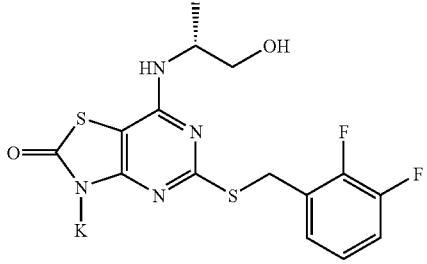

To a stirred suspension of 5-[[(2,3-difluorophenyl)methyl]thio]-7-[[(1R)-2-hydroxy-1-methylethyl]amino]-3-[2-(phenylsulfonyl)ethyl]thiazolo[4,5-d]pyrimidin-2-(3H)-one (2.0 g, 1.0 eq), as prepared in Example 2(a) above, in propan-2-ol (25.5 ml) at room temperature under nitrogen, was added potassium t-butoxide (0.449, 1.05 eq). The resulting suspension was heated to an internal temperature of 75-78° C. (reflux). After 1.5 hours at this temperature, water (4.5 ml) was added and the reaction became a solution. The reaction was reheated to 75-78° C. before sampling for HPLC analysis. The sample showed almost complete consumption of the starting material (0.36% 5-[[(2,3-difluorophenyl)methyl]thio]-7-[[(1R)-2-hydroxy-1-methylethyl]amino]-3-[2-(phenylsulfonyl)ethyl]thiazolo[4,5-d]pyrimidin-2-(3H)-one remained). The reaction was allowed to cool, seeded at 50° C. with 5-[[(2,3-difluorophenyl)methyl]thio]-7-[[(1R)-2-hydroxy-1-methylethyl]amino]thiazolo[4,5-d]pyrimidin-2-(3H)-one, potassium salt (2 mgs) and then cooled to room temperature. The precipitate was 'aged' at room temperature for 1 hour before filtering. The cake was washed with propan-2-ol (3×4 ml). The white solid was collected and dried in a vacuum oven over night at 50° C. This process yielded 63% (0.96 g) of a white solid which was of high purity (99.65% by HPLC area).

¹H NMR: δ (DMSO-d6) 1.06 (d, 3H), 3.26-3.43 (m, 2H), 4.09 (quin, 1H), 4.34 (m, 2H), 4.65 (bs, 1H), 5.59 (d, 1H), 7.12 (q, 1H), 7.28 (q, 1H), 7.37 (t, 1H).

Alternatively, the compound of Example 1(e) may be reacted with potassium hydroxide to give the title compound.

EXAMPLE 3

5-[[(2,3-difluorophenyl)methyl]thio]-7-[[-2-hydroxy-1-(hydroxymethyl)-1-methylethyl]amino]thiazolo[4,5-d]pyrimidin-2(3H)-one, sodium salt (a) 5-[[(2,3-difluorophenyl)methyl]thio]-3-[2-(phenylsulfonyl)ethyl]-7-[(2,2,5-trimethyl-1,3-dioxan-5-yl)amino]thiazolo[4,5-d]pyrimidin-2(3H)-one

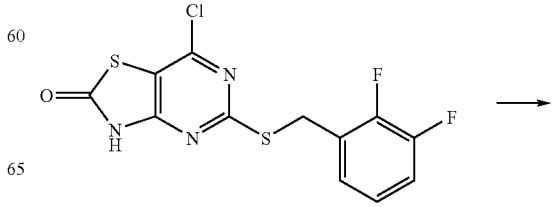

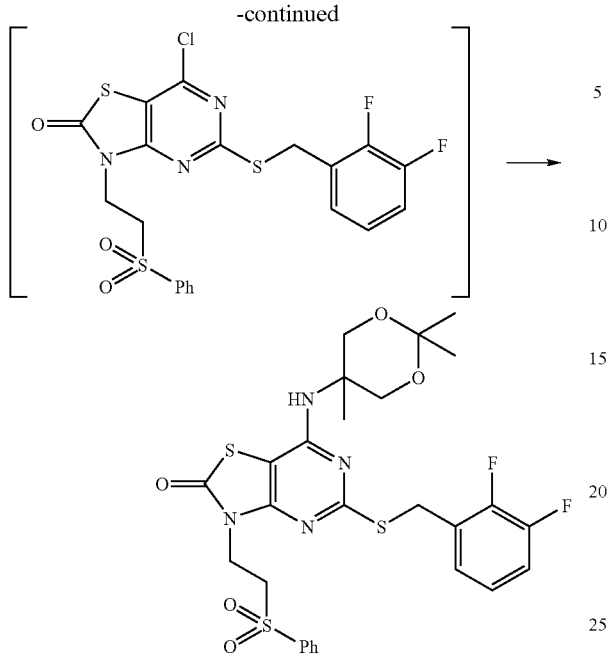

To a stirred suspension of 7-chloro-5-[[(2,3-difluorophenyl)methyl]thio]thiazolo[4,5-d]pyrimidin-2-(3H)-one, prepared as shown in Example 1, steps (a) to (c), (1.0 g, 1.0 eq) in butyronitrile (15 ml) at room temperature under nitrogen, was added diisopropylethylamine (0.5 ml, 1.0 eq), forming a solution. Phenylvinylsulfone (0.63 g, 1.3 eq) was added to the vessel. The orange solution was heated to an internal temperature of 100° C. After 18 hours HPLC showed almost complete consumption of the starting material (0.93% 7-chloro-5-[[(2,3-difluorophenyl)methyl]thio]thiazolo[4,5-a]pyrimidin-2-(3H)-one remained). At this point further diisopropylethylamine (0.5 ml, 1.0 eq) was added to the mixture at 50° C., followed by (2,2,5-trimethyl-1,3-dioxan-5-yl)amine (0.63 g, 1.5 eq). (2,2,5-trimethyl-1,3-dioxan-5-yl)amine is disclosed in J. Nat. Prod, 1999, 62, 963-968.

After over night stir at 100° C. HPLC showed incomplete consumption of the reaction intermediate (32.56% 7-chloro-5-[[(2,3-difluorophenyl)methyl]thio]-3-[2-(phenylsulfonyl)ethyl]thiazolo[4,5-d]pyrimidin-2-(3H)-one remained). A further portion of (2,2,5-trimethyl-1,3-dioxan-5-yl)amine (0.21 g, 0.5 eq) was added. The reaction took another 4 days at 100° C. by which time the HPLC showed <10% of the intermediate (7.80% 7-chloro-5-[[(2,3-difluorophenyl)methyl]thio]-3-[2-(phenylsulfonyl)ethyl]thiazolo[4,5-a]pyrimidin-2-(3H)-one, as well as 13.42% of 5-[[(2,3-difluorophenyl)methyl]thio]-7-[[2-hydroxy-1-(hydroxymethyl)-1-methylethyl]amino]-3-[2-(phenylsulfonyl)ethyl]thiazolo[4,5-a]pyrimidin-2(3H)-one where the acetonide had cleaved in situ). The reaction was allowed to cool from 100 to 50° C. Whilst at 50° C. water (10 ml) was added. No precipitate was observed. The layers were separated, organic layer washed further with water (10 ml), dried over $MgSO_4$, filtered and evaporated to dryness to give an orange oil.

Purification was achieved by chromatography over silica eluting with 20-30% ethyl acetate/ihexane on silica to yield a white solid.

$^1$H NMR: δ (DMSO-d6) 1.27 (s, 3H), 1.33 (s, 3H), 1.36 (s, 3H), 3.67 (d, 2H), 3.82 (t, 2H), 4.14 (m, 4H), 4.38 (s, 2H), 7.20 (m, 2H), 7.34 (t, 2H), 7.54 (t, 2H), 7.66 (t, 1H), 7.81 (d, 2H).

(b) 5-[[(2,3-difluorophenyl)methyl]thio]-7-[[2-hydroxy-1-(hydroxymethyl-1-methylethyl]amino]-3-[2-(phenylsulfonyl)ethyl]thiazolo[4,5-d]pyrimidin-2(3H)-one

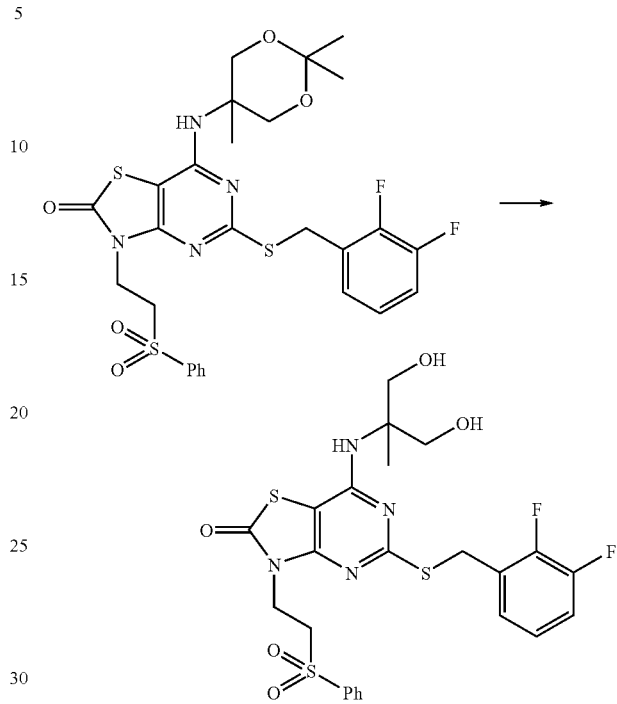

5-[[(2,3-difluorophenyl)methyl]thio]-3-[2-(phenylsulfonyl)ethyl]-7-[(2,2,5-trimethyl-1,3-dioxan-5-yl)amino]thiazolo[4,5-d]pyrimidin-2(3H)-one (0.19 g) was subjected to stirring under nitrogen with THF (2 ml), and 1M HCl (2 ml). After an hour stirring at room temperature HPLC revealed that the deprotection was complete (0.48% of the starting material remaining).

To the mixture was added i-propyl acetate (5 ml) and water (2 ml). The lower aqueous layer was removed and washed with a further two portions of i-propyl acetate (2×7.5 ml). Combined organics were washed twice with water (2×10 ml), dried over $MgSO_4$, filtered and evaporated to give a white solid with 88% yield (0.156 g).

$^1$H NMR: δ (DMSO-d6) 1.25 (s, 3H), 3.60 (m, 4H), 3.80 (t, 2H), 4.15 (t, 2H), 4.38 (s, 2H), 4.68 (t, 2H), 6.51 (s, 1H), 7.17 (m, 1H), 7.34 (t, 2H), 7.57 (t, 2H), 7.67 (t, 1H), 7.84 (d, 2H).

(c) 5-[[(2,3-difluorophenyl)methyl]thio]-7-[[-2-hydroxy-1-(hydroxymethyl)-1-methylethyl]amino]thiazolo[4,5-d]pyrimidin-2(3H)-one, sodium salt

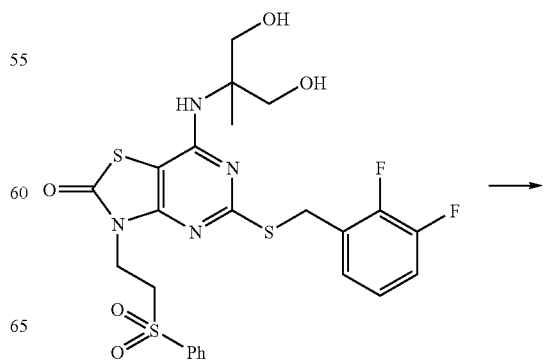

-continued

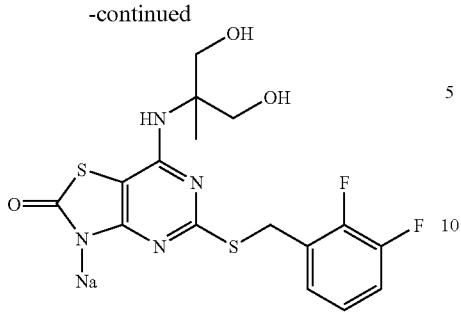

To 5-[[(2,3-difluorophenyl)methyl]thio]-7-[[2-hydroxy-1-(hydroxymethyl)-1-methylethyl]amino]-3-[2-(phenylsulfonyl)ethyl]thiazolo[4,5-d]pyrimidin-2(3H)-one (0.15 g, 1.0 eq) was added sodium t-butoxide (0.028 g, 1.1 eq). The two solids were purged with nitrogen. Propan-2-ol (2 ml) was added to give a suspension at room temperature. The reaction was heated to give a yellow solution. After 1 hour at reflux a sample was taken for HPLC analysis, which revealed completion (only 1.39% starting material remained). The reaction was cooled to room temperature and a precipitate was observed. The product was filtered and washed with propan-2-ol (~1 ml). The collected white solid was dried in a vacuum oven at 40° C. to yield 81% (0.091 g).

$^1$H NMR: δ (DMSO-d6) 1.22 (s, 3H), 3.40 (m, 2H), 3.56 (m, 2H), 4.35 (s, 2H), 4.80 (s, 1H), 5.05 (t, 2H), 7.17 (m, 1H), 7.36 (t, 2H).

EXAMPLE 4

5-[[(2,3-difluorophenyl)methyl]thio]-7-[[2-hydroxy-1-(hydroxymethyl)-1-methylethyl]amino]thiazolo[4,5-d]pyrimidin-2(3H)-one, potassium salt To 5-[[(2,3-difluorophenyl)methyl]thio]-7-[[2-hydroxy-1-(hydroxymethyl)-1-methylethyl]amino]thiazolo[4,5-a]pyrimidin-2(3H)-one (0.881 g, 2.13 mmol) in methanol (20 ml) was added KOMe (0.165 g, 2.34 mmol, 1.1 eq) and the mixture heated to reflux. Further methanol (10 ml) was added to obtain a solution. The solution was allowed to cool and the solvent removed on a rotary evaporator and the resultant solid dried in vacuo. This gave the title compound (0.828 g, 86%).

$^1$H NMR: δ (DMSO-d6) 1.25 (3H, s), 3.52 (2H, m), 3.62 (2H, m), 4.37 (2H, s), 4.8-5.2 (2H, broad s), 5.06 (1H, s), 7.15 (1H, m), 7.38 (2H, m)

Alternatively, the compound of Example 3(c) may be reacted with potassium t-butoxide to give the title compound.

The invention claimed is:

1. A method for the preparation of a compound of formula (I) or a pharmaceutically acceptable salt thereof:

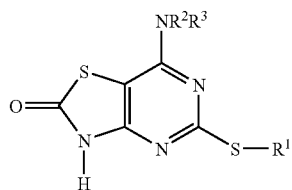

(I)

in which

R$^1$ represents a C$_3$-C$_7$ carbocyclic, C$_1$-C$_8$ alkyl, C$_2$-C$_6$ alkenyl or C$_2$-C$_6$ alkynyl group, each of the groups being optionally substituted by one or more substituent groups independently selected from halogen atoms, —OR$^4$, —NR$^5$R$^6$, —CONR$^5$R$^6$, —COOR$^7$, —NR$^8$COR$^9$, —SR$^{10}$, —SO$_2$R$^{10}$, —SO$_2$NR$^5$R$^6$, —NR$^8$SO$_2$R$^9$ or a phenyl group, a naphthyl group, or a 5- or 6-membered heteroaryl group containing one or more heteroatoms selected from N, S, and O, wherein the phenyl group, the naphthyl group, and the 5- or 6-membered heteroaryl group are each optionally substituted by one or more substituents independently selected from halogen atoms, cyano, nitro, —OR$^4$, —NR$^5$R$^6$, —CONR$^5$R$^6$, —COOR$^7$, —NR$^8$COR$^9$, —SR$^{10}$, —SO$_2$R$^{10}$, —SO$_2$NR$^5$R$^6$, —NR$^8$SO$_2$R$^9$, C$_1$-C$_6$ alkyl or trifluoromethyl groups;

R$^2$ and R$^3$ each independently represent a hydrogen atom, or a C$_3$-C$_7$ carbocyclic, C$_1$-C$_8$ alkyl, C$_2$-C$_6$ alkenyl or C$_2$-C$_6$ alkynyl group, the latter four groups may be optionally substituted by one or more substituent groups independently selected from:

(a) halogen atoms, —OR$^4$, —NR$^5$R$^6$, —CONR$^5$R$^6$, —COOR$^7$, —NR$^8$COR$^9$, —SR$^{10}$, —SO$_2$R$^{10}$, —SO$_2$NR$^5$R$^6$, —NR$^8$SO$_2$R$^9$;

(b) a 3-8 membered ring optionally containing one or more atoms selected from O, S, NR$^8$ and itself optionally substituted by C$_1$-C$_3$-alkyl or halogen; or (c) a phenyl group, a naphthyl group, or a 5- or 6-membered heteroaryl group containing one or more heteroatoms selected from N, S, and O, wherein the phenyl group, the naphthyl group, and the 5- or 6-membered heteroaryl group are each optionally substituted by one or more substituents independently selected from halogen atoms, cyano, nitro, —OR$^4$, —NR$^5$R$^6$, —CONR$^5$R$^6$, —NR$^8$COR$^9$, —SO$_2$NR$^5$R$^6$, —NR$^8$SO$_2$R$^9$, C$_1$-C$_6$ alkyl and trifluoromethyl groups;

R$^4$ represents hydrogen, C$_1$-C$_6$ alkyl or a phenyl group the latter two of which may be optionally substituted by one or more substituent groups independently selected from halogen atoms, phenyl, —OR$^{11}$ and —NR$^{12}$R$^{13}$ R$^5$ and R$^6$ independently represent a hydrogen atom or a C$_1$-C$_6$ alkyl or phenyl group the latter two of which may be optionally substituted by one or more substituent groups independently selected from halogen atoms, phenyl, —OR$^{14}$ and —NR$^{15}$R$^{16}$, —CONR$^{15}$R$^{16}$, —NR$^{15}$COR$^{16}$, —SONR$^{15}$R$^{16}$, NR$^{15}$SO$_2$R$^{16}$ or R$^5$ and R$^6$ together with the nitrogen atom to which they are attached form a 4- to 7-membered saturated heterocyclic ring system optionally containing a further heteroatom selected from oxygen and nitrogen atoms, which ring system may be optionally substituted by one or more substituent groups independently selected from phenyl, —OR$^{14}$, —COOR$^{14}$, —NR$^{15}$R$^{16}$, —CONR$^{15}$R$^{16}$, —NR$^{15}$COR$^{16}$, —SONR$^{15}$R$^{16}$, NR$^{15}$SO$_2$R$^{16}$ or C$_1$-C$_6$ alkyl, itself optionally substituted by one or more substituents independently selected from halogen atoms and —NR$^{15}$R$^{16}$ and —OR$^{17}$ groups;

R$^{10}$ represents a hydrogen atom or a C$_1$-C$_6$-alkyl or a phenyl group, the latter two of which may be optionally substituted by one or more substituent groups independently selected from halogen atoms, phenyl, —OR$^{17}$ and —NR$^{15}$R$^{16}$; and each of R$^7$, R$^8$, R$^9$, R$^{11}$, R$^{12}$, R$^{13}$, R$^{14}$, R$^{15}$, R$^{16}$, R$^{17}$ independently represents a hydrogen atom or a C$_1$-C$_6$ alkyl, or a phenyl group;

which method comprises contacting

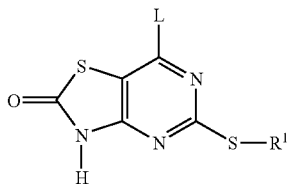

wherein L is a leaving group
with a thiazole nitrogen protecting group reagent under appropriate reaction conditions to form a compound of the formula

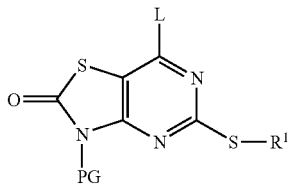

wherein PG is a protecting group,
reacting the compound of formula III with an amine of formula $HNR^2R^3$ to form a compound of formula

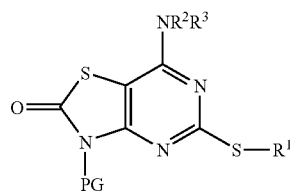

and deprotection of the compound of formula II to give a compound of the formula I, and simultaneous or sequential conversion to a pharmaceutically acceptable salt thereof.

2. A method as claimed in claim 1 and wherein $R^1$ represents an optionally substituted benzyl group.

3. A method as claimed in claim 1 and wherein one of $R^2$ or $R^3$ is hydrogen and the other is $C_1$-$C_8$ alkyl substituted by hydroxy and one or more methyl or ethyl groups.

4. A method as claimed in claim 1 for the preparation of a compound of the formula Ia

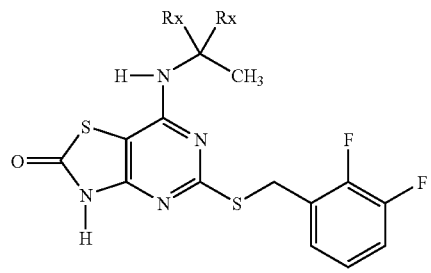

wherein each $R^X$ is independently selected from hydrogen, a $C_{1-4}$ alkyl group optionally substituted by hydroxy, amino, —O—$C_{1-4}$ alkyl, —S—$C_{1-4}$ alkyl, —N—$C_{1-4}$ alkyl, —NHSO$_2$R, or —CONR$_2$ and provided that both $R^X$ are not hydrogen or amino.

5. A method as claimed in claim 4 wherein each $R^X$ is independently selected from hydrogen and hydroxymethyl, provided that both $R^X$ are not hydrogen.

6. A compound of the formula

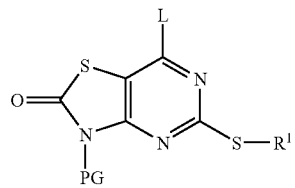

or a pharmaceutically acceptable salt thereof and wherein
$R^1$ represents a $C_3$-$C_7$ carbocyclic, $C_1$-$C_8$ alkyl, $C_2$-$C_6$ alkenyl or $C_2$-$C_6$ alkynyl group, each of the groups being optionally substituted by one or more substituent groups independently selected from halogen atoms, —OR$^4$, —NR$^5$R$^6$, —CONR$^5$R$^6$, —COOR$^7$, —NR$^8$COR$^9$, —SR$^{10}$, —SO$_2$R$^{10}$, —SO$_2$NR$^5$R$^6$, —NR$^8$SO$_2$R$^9$ or a phenyl group, a naphthyl group, or a 5- or 6-membered heteroaryl group containing one or more heteroatoms selected from N, S, and O, wherein the phenyl group, the naphthyl group, and the 5- or 6-membered heteroaryl group are each optionally substituted by one or more substituents independently selected from halogen atoms, cyano, nitro, —OR$^4$, —NR$^5$R$^6$, —CONR$^5$R$^6$, —COOR$^7$, —NR$^8$COR$^9$, —SR$^{10}$, —SO$_2$R$^{10}$, —SO$_2$NR$^5$R$^6$, —NR$^8$SO$_2$R$^9$, $C_1$-$C_6$ alkyl or trifluoromethyl groups;

$R^4$ represents hydrogen, $C_1$-$C_6$ alkyl or a phenyl group the latter two of which may be optionally substituted by one or more substituent groups independently selected from halogen atoms, phenyl, —OR$^{11}$ and —NR$^{12}$R$^{13}$ $R^5$ and $R^6$ independently represent a hydrogen atom or a $C_1$-$C_6$ alkyl or phenyl group the latter two of which may be optionally substituted by one or more substituent groups independently selected from halogen atoms, phenyl, —OR$^{14}$ and —NR$^{15}$R$^{16}$, —CONR$^{15}$R$^{16}$, —NR$^{15}$COR$^{16}$, —SONR$^{15}$R$^{16}$, NR$^{15}$SO$_2$R$^{16}$
or
$R^5$ and $R^6$ together with the nitrogen atom to which they are attached form a 4- to 7-membered saturated heterocyclic ring system optionally containing a further heteroatom selected from oxygen and nitrogen atoms, which ring system may be optionally substituted by one or more substituent groups independently selected from phenyl, —OR$^{14}$, —COOR$^{14}$, —NR$^{15}$R$^{16}$, —CONR$^{15}$R$^{16}$, —NR$^{15}$COR$^{16}$, —SONR$^{15}$R$^{16}$, NR$^{15}$SO$_2$R$^{16}$ or $C_1$-$C_6$ alkyl, itself optionally substituted by one or more substituents independently selected from halogen atoms and —NR$^{15}$R$^{16}$ and —OR$^{17}$ groups;

$R^{10}$ represents a hydrogen atom or a $C_1$-$C_6$-alkyl or a phenyl group, the latter two of which may be optionally substituted by one or more substituent groups independently selected from halogen atoms, phenyl, —OR$^{17}$ and —NR$^{15}$R$^{16}$;

each of $R^7$, $R^8$, $R^9$, $R^{11}$, $R^{12}$, $R^{13}$, $R^{14}$, $R^{15}$, $R^{16}$, $R^{17}$ independently represents a hydrogen atom or a $C_1$-$C_6$ alkyl, or a phenyl group;

L is a leaving group; and
PG is a protecting group.

7. A compound of the formula

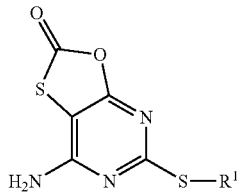

V or a pharmaceutically acceptable salt thereof and wherein $R^1$ represents a $C_3$-$C_7$ carbocyclic, $C_1$-$C_8$ alkyl, $C_2$-$C_6$ alkenyl or $C_2$-$C_6$ alkynyl group, each of the groups being optionally substituted by one or more substituent groups independently selected from halogen atoms, —$OR^4$, —$NR^5R^6$, —$CONR^5R^6$, —$COOR^7$, —$NR^8COR^9$, —$SR^{10}$, —$SO_2R^{10}$, —$SO_2NR^5R^6$, —$NR^8SO_2R^9$ or a phenyl group, a naphthyl group, or a 5- or 6-membered heteroaryl group containing one or more heteroatoms selected from N, S, and O, wherein the phenyl group, the naphthyl group, and the 5- or 6-membered heteroaryl group are each optionally substituted by one or more substituents independently selected from halogen atoms, cyano, nitro, —$OR^4$, —$NR^5R^6$, —$CONR^5R^6$, —$COOR^7$, —$NR^8COR^9$, —$SR^{10}$, —$SO_2R^{10}$, —$SO_2NR^5R^6$, —$NR^8SO_2R^9$, $C_1$-$C_6$ alkyl or trifluoromethyl groups;

$R^4$ represents hydrogen, $C_1$-$C_6$ alkyl or a phenyl group the latter two of which may be optionally substituted by one or more substituent groups independently selected from halogen atoms, phenyl, —$OR^{11}$ and —$NR^{12}R^{13}$ $R^5$ and $R^6$ independently represent a hydrogen atom or a $C_1$-$C_6$ alkyl or phenyl group the latter two of which may be optionally substituted by one or more substituent groups independently selected from halogen atoms, phenyl, —$OR^{14}$ and —$NR^{15}R^{16}$, —$CONR^{15}R^{16}$, —$NR^{15}COR^{16}$, —$SONR^{15}R^{16}$, $NR^{15}SO_2R^{16}$ or $R^5$ and $R^6$ together with the nitrogen atom to which they are attached form a 4- to 7-membered saturated heterocyclic ring system optionally containing a further heteroatom selected from oxygen and nitrogen atoms, which ring system may be optionally substituted by one or more substituent groups independently selected from phenyl, —$OR^{14}$, —$COOR^{14}$, —$NR^{15}R^{16}$, —$CONR^{15}R^{16}$, —$NR^{15}COR^{16}$, —$SONR^{15}R^{16}$, $NR^{15}SO_2R^{16}$ or $C_1$-$C_6$ alkyl, itself optionally substituted by one or more substituents independently selected from halogen atoms and —$NR^{15}R^{16}$ and —$OR^{17}$ groups;

$R^{10}$ represents a hydrogen atom or a $C_1$-$C_6$-alkyl or a phenyl group, the latter two of which may be optionally substituted by one or more substituent groups independently selected from halogen atoms, phenyl, —$OR^{17}$ and —$NR^{15}R^{16}$; and each of $R^7$, $R^8$, $R^9$, $R^{11}$, $R^{12}$, $R^{13}$, $R^{14}$, $R^{15}$, $R^{16}$, $R^{17}$ independently represents a hydrogen atom or a $C_1$-$C_6$ alkyl, or a phenyl group.

* * * * *

UNITED STATES PATENT AND TRADEMARK OFFICE
CERTIFICATE OF CORRECTION

Page 1 of 1

PATENT NO. : 7,790,883 B2
APPLICATION NO. : 10/581143
DATED : September 7, 2010
INVENTOR(S) : Michael Butters et al.

It is certified that error appears in the above-identified patent and that said Letters Patent is hereby corrected as shown below:

Front Page of Patent, left hand column, under the heading "Inventors;", "Colin Thompson" should read -- Colin Thomson --.

Front Page of Patent, left hand column, insert between fields (22) and (65): -- The application is a national phase application under 35 U.S.C. §371 of PCT International Application No. PCT/GB2004/005072, filed Dec. 2, 2004. --

Column 1, line 10, "Swedish" should read -- Great Britain --.

Column 1, line 12 (approximately), delete "METHODS".

Column 16, line 3, "—SR $^{10}$, —SO $_2$R$^{10}$," should read -- —SR$^{10}$, —SO$_2$R$^{10}$, --.

Column 16, line 12 (approximately), "—SR $^{10}$" should read -- —SR$^{10}$, --.

Column 16, line 21, "—SO $_2$R$^{10}$," should read -- —SO$_2$R$^{10}$, --.

Column 16, line 55 (approximately), "—NR $^{15}$R$^{16}$," and insert -- —NR$^{15}$R$^{16}$, --.

Column 17, lines 55-65 (approximately), formula Ia, those parts of the formula reading "$R_X$" should read -- $R^X$ --.

Column 18, line 3, "—O —C$_{1-4}$" should read -- —O—C$_{1-4}$ --.

Column 18, line 3, "—N —C$_{1-4}$" should read -- —N—C$_{1-4}$ --.

Signed and Sealed this
Twenty-fourth Day of July, 2012

David J. Kappos
*Director of the United States Patent and Trademark Office*